United States Patent [19]

Cullinan et al.

[11] Patent Number: 5,094,849
[45] Date of Patent: * Mar. 10, 1992

[54] CYTOTOXIC ANTIBODY CONJUGATES OF HYDRAZIDE DERIVATIZED VINCA ANALOGS VIA SIMPLE ORGANIC LINKERS

[75] Inventors: George J. Cullinan, Trafalgar; Bennett C. Laguzza; William L. Scott, both of Indianapolis, all of Ind.

[73] Assignee: Eli Lilly and Company, Indianapolis, Ind.

[*] Notice: The portion of the term of this patent subsequent to Jul. 2, 2008 has been disclaimed.

[21] Appl. No.: 640,792

[22] Filed: Jan. 14, 1991

Related U.S. Application Data

[62] Division of Ser. No. 230,084, Aug. 8, 1988, Pat. No. 5,006,652.

[51] Int. Cl.⁵ .................. A61K 39/44; C07K 17/02
[52] U.S. Cl. ........................... 424/85.91; 530/391.9; 530/408; 530/409
[58] Field of Search ............... 530/388, 390, 391, 408, 530/409; 424/85.91

[56] References Cited

U.S. PATENT DOCUMENTS

| | | | |
|---|---|---|---|
| 4,203,898 | 5/1980 | Cullinan et al. | 540/478 |
| 4,631,190 | 12/1986 | Shen et al. | 424/85.91 |
| 4,671,958 | 6/1987 | Rodwell et al. | 424/85.91 |
| 4,675,400 | 6/1987 | Cullinan | 540/478 |
| 4,801,688 | 1/1989 | Laguzza et al. | 530/391 |
| 4,828,831 | 5/1989 | Hannart et al. | 424/85.91 |

FOREIGN PATENT DOCUMENTS

| | | |
|---|---|---|
| 63401/86 | 9/1986 | Austria . |
| 0056322 | 7/1982 | European Pat. Off. . |
| 0088695 | 9/1983 | European Pat. Off. . |
| 0124502 | 4/1984 | European Pat. Off. . |
| 0243929 | 11/1987 | European Pat. Off. . |
| 0253202 | 1/1988 | |
| 326322 | 8/1989 | European Pat. Off. . |
| 121388 | 10/1984 | United Kingdom . |
| 2137210A | 10/1984 | United Kingdom . |

OTHER PUBLICATIONS

Blickenstaff, et al., *Chemical Abstracts*, vol. 94: 114277s (1981).
King et al., *Biochem.* 25, 5774–79 (1986).
Ghose et al., *Methods Enzymology* 93, 280–333 (1983).
Blair et al., *J. Immunol. Methods* 59, 129–43 (1983).
Shen et al., *Biochem. Biophys. Res. Comm.* 102, 1048–54 (1981).
Bumol et al., AACR Proceedings, Abstract 1410 (1984).
Bumol et al., *J. Cell Biochem.*, Supp. 9A, Abstract 0124 (1985).
Ghose et al., *CRC Critical Rev. in Therapeutic Drug Carrier Systems* 3, 263–359 (1987).
Bumol et al., Faseb 69th Annual Meeting, Abstract 8484 (1985).

*Primary Examiner*—Jeffrey E. Russel
*Assistant Examiner*—Kay Kim
*Attorney, Agent, or Firm*—Joseph A. Jones; Leroy Whitaker

[57] ABSTRACT

A series of antibody-vinca drug conjugates comprise antibodies which target antigens associated with undesirable cells, so that the cells are controlled or killed by the cytotoxic vinca drug. The drug is linked to the antibody through an organic group comprising a carbonyl at the antibody end, and an alkylidene hydrazide at the vinca end.

22 Claims, No Drawings

CYTOTOXIC ANTIBODY CONJUGATES OF HYDRAZIDE DERIVATIZED VINCA ANALOGS VIA SIMPLE ORGANIC LINKERS

This application is a division of application Ser. No. 07/230,084, filed Aug. 8, 1988, U.S. Pat. No. 5,006,652, issued Apr. 9, 1991.

FIELD OF THE INVENTION

The present invention belongs to the fields of organic chemistry, immunology, and pharmaceutical chemistry, and provides cytotoxic drug conjugates useful for the targeted administration of cytotoxic drugs to patients in need of such treatment. Targeting of the drug conjugates is obtained by the use of antibodies which recognize an antigen associated with the cell to be treated with the cytotoxic drug, and thereby carry the cytotoxic drug to the cell. Intermediates used in the synthesis of the conjugates are also provided.

BACKGROUND OF THE INVENTION

As long ago as 1900, Ehrlich proposed that drugs might be guided to the target organ by attaching the drugs to substances which would seek that target organ. The technology to follow up on Ehrlich's suggestion did not exist until monoclonal antibody technology began to appear in the 1970's. For some years now, publications on the targeting of drugs with the aid of antibodies have been regularly appearing. However, as yet, no antibody-conjugated drug is approved for therapeutic use. Chemists and immunologists continue to experiment, seeking a method of making antibody-drug conjugates which will transport the drug reliably to the target organ and release it at the proper time. It has been found, however, that many such conjugates, although comprised of a known drug and an active antibody, are relatively ineffective. Such failures may be caused by chemical damage to the drug or the antibody, or the antibody's failure to release the drug at the right time and place.

The present invention provides a series of vinca drug conjugates linked to antibodies by means of a linker system which gives particularly good release of the drug, in a physiologically active form.

SUMMARY OF THE INVENTION

The present invention provides a cytotoxic drug conjugate of the formula

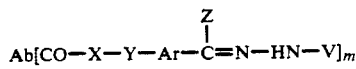

wherein Ab is a physiologically-acceptable antibody or antigen-recognizing fragment thereof, which recognizes an antigen associated with an undesirable cell;
  m is an integer from 1 to about 10;
  Z is hydrogen or $C_1$-$C_3$ unbranched alkyl;
  X is a bond, $C_1$-$C_4$ alkylene, $C_2$-$C_4$ alkenylene, or amino-$C_1$-$C_4$ alkylene;
  Y is a bond, carbonyl —O—, —S—, or sulfonyl, provided that Y is carbonyl or sulfonyl when X is aminoalkylene, and that Y is a bond or carbonyl when X is a bond;
  Ar is pyrrolyl, m-phenyl, or p-phenyl, which phenyl groups may be mono- or disubstituted with bromo, chloro, fluoro, methoxy, nitro or $C_1$-$C_3$ alkyl;

V is a vinca drug of the formula

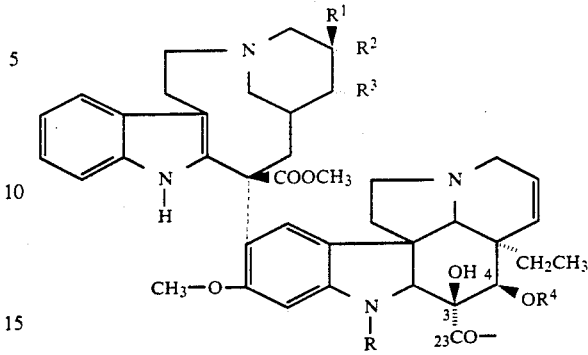

wherein R is H, $CH_3$ or CHO; when $R^2$ and $R^3$ are taken singly, $R^3$ is H, and one of $R^1$ and $R^2$ is ethyl and the other is H or OH; when $R^2$ and $R^3$ are taken together with the carbons to which they are attached, they form an oxirane ring in which case $R^1$ is ethyl; $R^4$ is H, ($C_1$-$C_3$ alkyl)-CO, or chlorosubstituted ($C_1$-$C_3$ alkyl)-CO.

The present invention also provides novel intermediates for preparing the above conjugates, which intermediates are of the formula

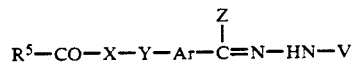

wherein $R^5$ is hydroxy, an acid-activating group, a moiety which completes a salt, or an acid-protecting group, and the other variable groups are as defined above.

The invention also provides a method of controlling the growth of undesirable cells by administering a conjugate of the invention parenterally to the patient. A further aspect of the invention is a pharmaceutical therapeutic composition comprising a conjugate of the invention dispersed in a parenterally administrable medium.

DETAILED DESCRIPTION OF THE INVENTION

The present vinca drug conjugates are composed of an antibody, a linker and a vinca drug in the hydrazide form. The remarkable therapeutic properties of the conjugates are primarily derived from the properties of the linker, which is so designed as to release the vinca drug from the antibody in a manner which gives maximum toxicity of the drug to target cell. The three major components of the conjugates will be discussed individually, the synthesis of the conjugates will be explained, and, finally, examples of the synthesis and biological efficacy of the conjugates will be shown.

The Antibody

The essential property of the antibody portion of the conjugates is its ability to recognize an antigen associated with an undesirable cell. It will be understood that the vinca drugs are highly cytotoxic to a wide variety of cells. Thus, the antibody is chosen for its ability to recognize and bind to the cell which is to be killed or otherwise controlled with the drug.

The source of the antibody is not critical to the present invention. It may be chosen from any class or subclass of immunoglobulin including IgG, IgA, IgM, IgE and IgD. Similarly, the species of origin is not critical so long as the antibody targets a cell where the effect of the vinca drug is useful.

In the present state of the art, monoclonal antibodies are most used in drug conjugates, and use of them is preferred in the present invention. However, polyclonal antibodies are not excluded. A newer type of antibody is the chimeric antibody, which is prepared in the laboratory by recombinant technology which permits expression of a modified DNA which encodes the antigen-binding region of any desired antibody, and also encodes any other desired amino acid sequence. Thus, chimeric antibodies of which one portion is derived from one species, and another portion is derived from another species may be obtained and used in the present invention. Use of chimeric antibodies is also preferred.

The origin and nature of the antibody is not otherwise critical, so long as it targets the cell to be treated and does not make the conjugate unacceptably toxic. Those of ordinary skill, using the present disclosure, can readily prepare conjugates with a candidate antibody and evaluate them. Some discussion of the method of evaluating antibodies and conjugates will be provided for convenience. First, the antibody should be produced by a hybridoma which is sufficiently stable to allow preparation of reasonable quantities of antibody. The antibody itself should be amenable to the conjugation reactions and to purification, and in particular should be sufficiently water-soluble to allow chemical manipulations at reasonable concentration.

Conjugates prepared with the candidate antibody are first evaluated for antigen-binding capacity. A modest reduction from the binding capacity of the free antibody is expected and acceptable. Then, the conjugate is tested to determine its in vitro cytotoxicity, against antigen positive cells. An effective conjugate can have cytotoxicity somewhat less than the free drug in the same assay. A conjugate which is accepted in the first two tests is then evaluated in a nude mouse human tumor xenograft model, as taught by Johnson and Laguzza, *Cancer Res.* 47, 3118–22 (1987). The candidate conjugate should be tested in nude mice against the free drug, a mixture of free drug and free antibody, and a conjugate with a non-targeting immunoglobulin, and should be more effective or safer than all. Dose ranging and timing studies should be carried out in the xenograft model.

Conjugates which are effective in the xenograft model are submitted to tests in animals which are known to express the antigen of interest in a pattern similar to that seen in humans. If the conjugate produces a significant degree of binding to the antigen in such tests, and if it is reasonably free of toxicity at doses predicted by the xenograft model to be therapeutic, the candidate conjugate can be considered to have therapeutic potential.

Many presently known antibodies are available for use in the present invention. An interesting specific antibody is L/1C2, which is produced by a hybridoma on deposit in the American Type Culture Collection, Rockville, Md., as HB9682.

Antibody 5E9C11, produced by an ATCC hybridoma, HB21, recognizes transferrin receptor, which is expressed by many tumors. An antibody called B72.3, available from the National Cancer Institute, recognizes antigens expressed by both breast and colon carcinoma.

Two interesting antibodies with reactivities against non-tumor antigens are OKT3 and OKT4, which bind to peripheral T-cells and human T-helper cells, respectively. They are produced by hybridomas on deposit in the ATCC as CRL8001 and CRL8002, respectively.

Additional sources of antibodies useful for various therapeutic purposes are the following. Anti-human lymphocyte and monocyte antibodies, useful for immune modulation and tumor therapy, are produced by ATCC cultures HB2, HB22, HB44, HB78 and HB136. An anti-transferrin receptor antibody, useful for tumor therapy, is produced by ATCC culture HB84. ATCC culture HB8059 produces an antibody against colorectal carcinoma monosialoganglioside, and culture HB8136 produces an antibody against mature human T-cell surface antigen, useful for immune modulation and T-cell leukemia therapy.

Further candidate antibodies are readily located by those of skill in the art. A particularly useful source of information about readily available antibodies is Linscott's Directory of Immunological and Biological Reagents, published by Linscott's Directory, 40 Glen Drive, Mill Valley, Calif. 94941. The 1984 edition lists more than 60 tumor-associated monoclonal antibodies, and at least one commercial source for each.

It will be understood that a variety of undesirable cells may be treated with conjugates of the present invention. The vinca drugs are well known to be effective against various types of cancer, and it is contemplated that cancer cells are among the preferred cells to be targeted by the present conjugates.

In particular, cells which support continued development of a malignancy, and cells of the immune system which control development of anti-tumor immunity are also contemplated. Specific types of cancer-related cells to be targeted include squamous carcinoma cells, adenocarcinoma cells, small cell carcinoma cells, glioma cells, melanoma cells, renal cell carcinoma cells, transitional cell carcinoma cells, sarcoma cells, cells of supporting tumor vasculature, and cells of lymphoid tumors such as leukemias and lymphomas.

However, the vinca drugs are also cytotoxic to many other types of cells. Thus, the conjugates can be used, by proper choice of the antibody, to kill or drastically modify such undesirable cells as, for example, cells infected with virus particles, T cells infected with various harmful agents, and cells of the immune system which promote or control development of autoimmune diseases.

It will be understood that properly chosen fragments of antibodies have the same effect as the intact antibody. Thus, in the practice of this invention, antibody fragments, preferably F(ab')$_2$ fragments, which recognize an antigen associated with the cell to be treated, are just as useful as are intact antibodies.

The exact mechanism by which the linker group reacts with and attaches to the antibody is not shown in formula I, and is not perfectly known. The reaction is an acylation, as is demonstrated below, and a number of locations on antibody molecules are subject to acylation. Most commonly, acylations of antibodies are thought to proceed on the free amino groups of lysine moieties. However, the acylation can also attack hydroxy groups, phenol groups, imidazole rings and perhaps other moieties.

Formula I indicates that from 1 to about 10 linker-drug moieties are attached to each molecule of antibody. Of course, the number of such moieties per antibody molecule is an average number because a given batch of conjugate will necessarily contain molecules having a range of ratios of drug-linker to antibody. The most efficient use of the expensive antibody is obtained, of course, when a number of molecules of drug are attached to each antibody molecule. However, the attachment of an excessive number of molecules of drug-linker moiety usually has an adverse effect on the antibody's ability to recognize and bind to its antigen, and on water-solubility, so a compromise value for m must be found. In general, the preferred value for m is from about 4 to about 10. From about 3 to about 8 is another preferred value.

The Vinca Drug

The vinca drugs have been the object of pharmaceutical and medical research for some years. A great many have been studied, described in the literature, and patented, and a few have been approved for treatment of human cancer. The vinca drugs used in the present conjugates are, in themselves, known to the pharmaceutical art and can readily be obtained and used by the artisan. Some discussion of the drugs will be given, for the convenience of the reader.

In formula II above, where R is methyl, $R^1$ is hydroxyl, $R^2$ is ethyl, $R^3$ is H, and $R^4$ is acetyl, VLB (vinblastine) is represented; where R is formyl, $R^1$ is hydroxyl, $R^2$ is ethyl, $R^3$ is H and $R^4$ is acetyl, vincristine (VCR) is represented; where R is methyl, $R^1$ is ethyl, $R^2$ is hydroxyl, $R^3$ is H and $R^4$ is acetyl, leurosidine is represented; where R is methyl or formyl, $R^1$ is ethyl, $R^2$ and $R^3$ taken together with the carbons to which they are attached form an alpha-epoxide ring and $R^4$ is acetyl, leurosine and leuroformine, respectively, are represented; where R is methyl, $R^1$ is ethyl, $R^2$ and $R^3$ are H and $R^4$ is acetyl, deoxy VLB "B" (4'-deoxyleurosidine or 4'-epideoxy VLB) is represented; where R is methyl, $R^2$ is ethyl, $R^1$ and $R^3$ are H and $R^4$ is acetyl, deoxy VLB "A" or 4'-deoxy VLB is represented; and where R is CHO, $R^1$ is ethyl, $R^2$ and $R^3$ are H and $R^4$ is acetyl, 4'-epideoxyvincristine (1-formyl-1-desmethyl-4'-deoxyleurosidine) is represented.

The vinca drugs are converted to the hydrazides used in the conjugates of this invention by the procedure of U.S. Pat. No. 4,203,898, col 12, line 65 et seq. and Example 3, col 18. In this procedure, anhydrous hydrazine is reacted with the appropriate vinca alkaloid in ethanol in a sealed tube at about 60° C. The product of this reaction is a 4-desacetyl 3-carboxhydrazide since the acetoxy group at C-4 is hydrolyzed under the basic reaction conditions. If it is desirable to prepare an ester at C-4 ($R^4$ in II is ($C_1$–$C_3$ alkyl)-CO or chloro ($C_1$–$C_3$-alkyl)-CO), the above desacetyl C-3 carboxhydrazide is first protected by reaction with acetone to form an $N^2$-propylidene derivative. With the acylable $NH_2$ group of the hydrazide effectively protected against acylation, this protected derivative can then be acylated in routine fashion with an acyl halide (chloroacetyl chloride for example) or an acyl anhydride (propionic anhydride for example). The protecting group can then be removed by treatment with acid. If acylation also occurs on the C-3 hydroxyl, as it usually does, this C-3 acyl group can be preferentially removed by treatment with wet silica gel—see Hargrove, U.S. Pat. No. 3,392,173.

The following list illustrates some of the preferred vinca drugs of Formula II which may be employed in the conjugates and their common names as known in the art:

4-Desacetyl-VLB-3-carboxhydrazide ($R^4 = R^3$ = hydrogen; R = methyl; $R^1$ = hydroxy; $R^2$ = ethyl)

4-Desacetyl-VCR-3-carboxhydrazide ($R^4 = R^3$ = hydrogen; R = CHO; $R^1$ = hydroxy; $R^2$ = ethyl)

4-Desacetyl-4'-epidoxy-VLB-3-carboxhydrazide ($R^4 = R^2 = R^3$ = hydrogen; R = methyl; $R^1$ = ethyl)

4-Desacetyl-VLB-4-propionyl-3-carboxhydrazide ($R^4 = COCH_2CH_3$; R = methyl; $R^1$ = hydroxy; $R^2$ = ethyl; $R^3$ = hydrogen).

The Linker

The linker group, X-Y-Ar-C(Z), is an organic group which is bonded to the carbonyl at one end, and to the hydrazide at the other. The bond to the vinca hydrazide is an alkylidene hydrazide bond. It will be understood, however, that the bond may exist in other forms in solution, particularly in physiological solution. The double bond can be opened, allowing functional groups or protons to bond to the nitrogen and carbon atoms. As a result, a hydroxy group or other oxygen-linked species may attach to one side of the former double bond, and amino-linked moieties may do so as well. Water can weakly bond to one of the atoms. A moiety of the antibody also can form a weak bond to one of the atoms, and more than one of such reactions may occur, forming mixtures. Such products are transitory, however, and throughout this document the conjugate will be described as in the alkylidene hydrazide form, because that is the general and stable form of them.

The group X may be nothing more than a bond, or may be $C_1$–$C_4$ alkylene, such as methylene, ethylene, butylene, 2,2-propylene, isobutylene, or 1,2-dimethylethylene; it may be $C_2$–$C_4$ alkenylene, such as vinyl, allyl or 2-methylallyl; or it may be amino-$C_1$–$C_4$ alkylene, such as aminomethylene, aminoethylene, amino-3-methylpropylene, amino-1,1-dimethylethylene and the like. When X is aminoalkylene, the amino group is adjacent to the group Y. Preferred X groups include a bond, $C_1$–$C_2$ alkylene, and amino-$C_1$–$C_3$ alkylene, such as methylene, ethylene, aminomethylene and aminopropylene.

The group Y is a bridging group which may be only a bond, or may be carbonyl, sulfonyl, oxygen or sulfur. Preferred Y groups are a bond, oxygen, and carbonyl.

The groups X and Y are inter-related, and not all Y groups can be associated with certain X groups. When X is aminoalkylene, Y is only carbonyl or sulfonyl; and when X is a bond, Y is only a bond or carbonyl.

The group Ar is pyrrolyl or phenyl. A phenyl group is linked at the meta or para position, and the phenyl groups may be unsubstituted, or mono or disubstituted with named groups. Typical substituted Ar groups include 2-bromo-m-phenyl, 3-chloro-p-phenyl, 2,5-difluoro-p-phenyl, 3-methoxy-5-chloro-p-phenyl, 2,6-dinitro-m-phenyl, 3-propyl-p-phenyl, 2-methyl-5-fluoro-m-phenyl and the like. Preferred Ar groups include unsubstituted phenyl, particularly p-phenyl, and monosubstituted phenyl, particularly mono-substituted p-phenyl, as well as pyrrolyl.

The pendant group Z may be hydrogen, or a $C_1$–$C_3$ straight alkyl group including methyl, ethyl and propyl. Preferred Z groups are hydrogen and methyl.

The following group of exemplary linker groups, X-Y-Ar-C(Z), are named in order to illustrate further the conjugates of the present invention. In each case, the linker groups are named by beginning at the C(Z) end of the linker, and proceeding to the carbonyl end, regardless of the rules of nomenclature, in order to name the groups consistently.

2-Methylidenylpyrrol-5-yl
1-(3-Methylidenylpyrrol-4-yl)acetyl
1-(2-Methylidenylpyrrol-4-yloxy)ethylenyl
1-[2-(1,1-Ethylidenyl)pyrrol-5-ylthio]-2-methylethylenyl
1-(3-Methylidenylphenyl)-2-methylpropylenyl
1-(2,6-Dichloro-4-methylidenylphenylthio)ethenylenyl
1-[2,4-Dimethyl-3-(1,1-propylidenyl)phenoxy]-2-propenylenyl
1-[3-Bromo-4-(1,1-butylidenyl)phenyl]-3-pentenoyl
4-Methylidenyl-2-nitro-4-benzamidomethylenyl
1-(4-Methylidenylphenylsulfonamido)ethylenyl
1-(3-Methoxy-4-methylidenylphenylsulfonamido)-3-methylpropylenyl Preferred linker groups used in the present conjugates are 4-benzylidenyl, 1-(4-methylidenylbenzamido)ethylenyl, 1-(4-methylidenylphenyl)ethenyl, 4-methylidenylphenoxymethylenyl, 1-(2-methylidenylpyrrol-5-yl)ethylenyl, and 1-[4-(1,1-ethylidenyl)phenoxy]acetyl.

The Intermediates

The present intermediates are the reactants which are reacted with the antibody to prepare the conjugates. They are made up of the vinca hydrazide and the linker moiety, terminated by a carboxylic acid or modified carboxylic acid. The variable groups which make up the intermediates have been discussed above, except for the terminal $R^5$ group. $R^5$ may be hydroxy, forming the acid, or may be a carboxylic acid activating group, as discussed below in the Synthesis section. It may also be a salt-forming moiety, such as an alkali metal ion, an alkaline earth metal ion, or an amino group such as diethylamino, diethanolamino, and the like. It may also be an acid- protecting group, as taught by, for example, Greene, Protective Groups in Organic Synthesis, Wiley, New York, 1981, pp. 152-92. Such protective groups include esters, amides and hydrazides, particularly $R^5$ groups such as phenacyloxy, trichloroethoxy, t-butoxy, triphenylmethoxy, trimethylsilyloxy, stannyl esters, dimethylamino and the like.

Preferred intermediates are those comprising the preferred X, Y and Ar groups as discussed above. The preferred intermediates for reaction are those wherein $R^5$ is an acid activating group; those wherein $R^5$ is in other forms are useful as intermediates for preparation of the activated forms.

The intermediates also are useful as anticancer agents in their own right, and are administered for that purpose in the same manner and in similar dosages as the vinca drugs which they comprise.

Synthesis

The conjugates of the present invention are prepared by processes which are, individually, carried out according to principles presently known in the art. The primary consideration in processes involving antibodies is, of course, to preserve the structure and function of the antibody as much as possible, and to allow for purification of the intermediate products and final product. Within those principles, it is possible to carry out the reaction steps in either major order—that is, one may attach the linker to the antibody, and then react the vinca hydrazide with the linker, or react the linker and vinca hydrazide and attach the resulting intermediate to the antibody as the second step.

Preparation of the starting compounds from which the linker groups are derived is accomplished according to routine organic chemical processes. Many of those compounds are commercially obtainable, and the rest can be prepared by organic chemists of ordinary skill.

The synthesis of the intermediates and conjugates of the present invention is represented schematically as follows

SCHEME A

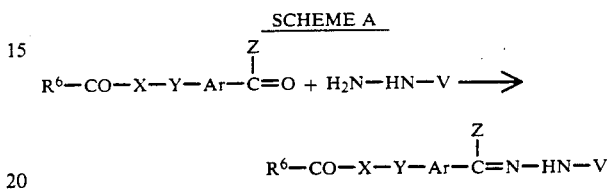

wherein $R^6$ is an acid protecting group, hydroxy or a moiety which completes a salt; and the ketone or aldehyde may be in the form of a dimethyl or diethyl acetal;

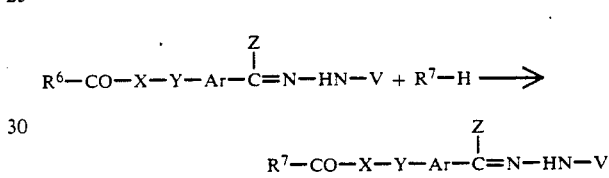

wherein $R^7$ is an acid activating group as described below;

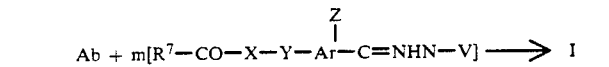

SCHEME B

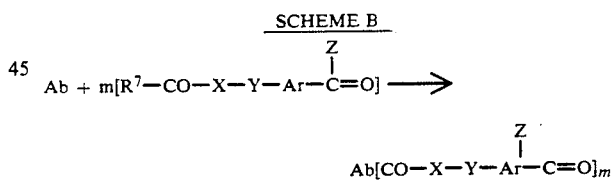

wherein the ketone or aldehyde may be in the form of a dimethyl or diethyl acetal;

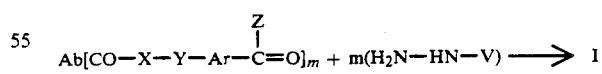

The vinca hydrazide, V—NH—NH$_2$, may be used as the base, or as an acid addition salt thereof. Sulfate salts are particularly convenient. However, the usual acid addition salts may be made and provide convenient forms of the vinca hydrazide for further synthesis. For example, salts such as hydrochlorides, hydrobromides, toluenesulfonates, methanesulfonates, benzoates, maleates, nitrates, phosphates and the like may be used as are convenient in particular reaction conditions.

The group $R^7$ is a carboxylic acid activating group, which is chosen from among well-known groups frequently used to activate carboxylic acids for use as acylation reagents. Activating groups used in peptide chemistry are particularly useful here. For example, groups such as succinimidoxy, phthalimidoxy, methanesulfonyloxy, toluenesulfonyloxy, benzenesulfonyloxy, benzotriazolyloxy, chloro, bromo, azido and the like are commonly used as such activating groups. The preferred carboxylic acid activating groups are succinimidoxy, phthalimidoxy and benzotriazolyloxy.

The carboxylic acid activating groups are readily placed on the carboxylic acids of the starting compounds ($R^6$—CO—X—Y—Ar—(Z)C=O) or the intermediates by use of, for example, dicyclohexylcarbodiimide or other typical esterification reagents. Such reactions are carried out in inert organic solvents such as dioxane, tetrahydrofuran, chlorinated hydrocarbons and the like, and may be performed at moderate temperatures in the range of about 0°–50° C. Preparation of the activated linker intermediates is further explained below in the Preparations.

The various steps of the synthesis of the present conjugates can be operated to maximize throughput of the equipment in which the process is carried out, or to maximize yield. In most if not all cases, the antibody itself represents the largest cost in the process, and therefore optimization of the process calls for maximizing yield based on the antibody. The optimum operating conditions, therefore, will depend on the conditions of maximum stability of the particular antibody in use. Further, maximization of yield based on the antibody usually infers that the last step of the process should be the reaction of the antibody with the intermediate. It is probable that optimum operating conditions will demand the use of a substantial excess of linker intermediate in order to maximize the utilization of the antibody and, to a somewhat lesser extent, the utilization of the expensive vinca drug.

The primary concern in choosing the conditions under which to react the intermediate or the activated linker intermediate with the antibody is maintaining the stability of the antibody. Accordingly, the reaction is carried out in aqueous medium of a composition which will not harm the antibody. A particularly suitable aqueous medium is a borate buffer in which the concentration of borate ion is in the range of about 0.1–0.5 molar. The pH of the reaction medium should be neutral to slightly basic, in the range, for example, of about 7 to 9. While the reaction medium is aqueous, the presence of small amounts of organic solvents is not harmful, and may be quite convenient. For example, it may be advantageous to dissolve the intermediate or linker intermediate in a small amount of organic solvent and add the organic solution to the aqueous antibody solution. Appropriate organic solvents for such use include, for example, dimethylformamide, tetrahydrofuran, dioxane or a glycol ether.

In general, it is necessary to operate the reaction at a low concentration, because the solubility of antibodies is generally not great. For example, the concentration of the antibody usually is in the range of about 5–25 mg per ml of aqueous medium.

As described above, from 1 to about 10 moles of linker and drug are attached to each mole of antibody. In order to obtain that conjugation ratio, it is usually necessary to use an excess quantity of linker intermediate or intermediate. The reactivity of antibodies under acylating conditions is somewhat variable, but, in general, from about 5 to about 30 moles of linker intermediate or intermediate per mole of antibody are used in the process.

The acylation of the antibody is allowed to proceed from a few minutes to a few hours, at temperatures in the range from about 0° to about 40° C. The reaction is inherently rather quick, and so it is usually possible to obtain acceptable throughput of the process at relatively low temperatures at which the antibody is acceptably stable. The conjugates of the present invention, and the various intermediate products containing the antibody are conveniently purified by chromatography according to conventional procedures. The Preparations and Examples below illustrate typical purifications. Progress of the reactions involving antibodies can be followed by dual wavelength ultraviolet analysis, as is usual in analyzing antibody-drug conjugates.

The chromatographic purifications may be carried out by eluting with dilute aqueous buffers, which may well be the same aqueous buffers used as aqueous reaction media in subsequent steps.

The reaction of the vinca hydrazide, V—NH—$NH_2$, with the linker intermediate is a quick and facile one which goes well at approximately ambient temperature in aqueous media such as have been discussed above, when the reaction is done as the second step according to Scheme B. A particular useful medium is dilute acetate buffer, especially 0.1 molar sodium acetate at a slightly acid pH, such as about 5–7. Other slightly acid buffers may also be used, such as borate, slightly acidic phosphate buffers, physiological buffered saline and the like. When the reaction is done as the first step, according to Scheme A, it may be carried out more efficiently in organic solvents, such as tetrahydrofuran, dioxane, dimethylformamide and the like. Reactions of the vinca drugs should be carried out in the dark.

The synthesis of the present conjugates is further explained by the following Preparations and Examples.

PREPARATION 1

4-desacetyl-23-desmethoxyvinblastine, 4-carboxybenzylidenehydrazide

A 1.3 g portion of 4-desacetyl-23-desmethoxyvinblastine, hydrazide was dissolved in 50 ml of tetrahydrofuran, and to it were added 5 g of anhydrous sodium sulfate and 2 g of 4-carboxybenzaldehyde. The mixture was stirred for two days under nitrogen at ambient temperature, and was then filtered and evaporated to dryness under vacuum. The residue was dissolved in 50 ml of dichloromethane and was washed twice with water. The organic layer was then dried over sodium sulfate, and was purified by high performance liquid chromatography, using a silica gel column and eluting with 8 liters of solvent which varied in a linear manner from 95:5 ethyl acetate: methanol to 1:1 ethyl acetate:-methanol. The product-containing fractions were combined and evaporated to dryness under vacuum to obtain 490 mg of the title compound, which was identified by mass spectroscopy, indicating a molecular ion of weight 900.

PREPARATION 2

4-desacetyl-23-desmethoxyvinblastine, 4-(N-succinimidoxy)carbonylbenzylidenehydrazide A 247 mg portion of the intermediate of Preparation 1 was added to 63 mg of N-hydroxysuccinimide and 8 ml of dichloromethane was added. The mixture was stirred for five minutes, and then 113 mg of dicyclohexylcarbodiimide was added, followed by 52 mg of p-toluenesulfonic acid. The mixture was stirred for one hour in all, and it was then cooled in an ice bath and extracted twice with 3 ml portions of 0.05M monobasic potassium phosphate buffer at pH 7. The organic layer was dried over sodium sulfate, and was then chromatographed over silica gel, eluting with 95:5 chloroform:methanol. The product-containing fractions were combined and concentrated under vacuum to obtain 227 mg of the desired intermediate.

EXAMPLE 1

Conjugate of Antibody 007B with 4-desacetyl-23-desmethoxyvinblastine, carbonyl-4-benzylidenehydrazide Antibody 007B is produced by a hybridoma which is a subclone derived from the hybridoma producing the antibody KS1/4, which was described by Varki et al., *Cancer Research* 44, 681-86 (1984). A portion of 007B was dialyzed into pH 8.6, 0.34M borate buffer, at a concentration of 10.3 mg/ml. To a 19.4 ml portion of the antibody solution was added, dropwise, 13 mg of the intermediate of Preparation 2, in the form of 1.6 ml of solution in dimethylformamide. The mixture was stirred at ambient temperature in the dark for 2 hours, and it was then centrifuged. The supernatant was gel filtered over Sephadex G25 (Pharmacia, Piscataway, N.J.), eluting with physiological buffered saline at pH 7.4. The eluant was filtered through 0.2 μm porous membrane, and was analyzed by ultraviolet analysis. Thirty-five ml of product solution was obtained, containing 3.36 mg/ml of conjugate at a conjugation ratio of 4.1 moles of vinca drug per mole of antibody.

The conjugate was tested in vivo against xenografts of the UCLA/P3 lung adenocarcinoma in female Charles River nude mice. The test was begun by implanting each mouse with $10^7$ UCLA/P3 tumor cells, subcutaneously. On each of days 2, 5 and 8 after implantation, each mouse was injected with the conjugate or with the intermediate of Preparation 2 in physiological buffered saline. Control mice were injected with saline only. The doses of conjugate or of vinca intermediate (based on vinca hydrazide content) are indicated below. The size of the tumors induced by implantation was measured on days 14, 21 and 28 after implantation. Each treatment group consisted of five mice, except for the untreated control group, which consisted of ten mice. The 28-day results are reported below.

TABLE I

| Treatment | Dose mg/kg | % Inhibition |
|---|---|---|
| Example 1 | 1.5 | 100 |
| | 0.75 | 100 |
| | 0.38 | 100 |
| | 0.19 | 71 |
| | 0.10 | 55 |
| Preparation 2 | 1.5 | 28 |
| | 0.75 | 11 |
| | 0.38 | 0 |
| | 0.19 | 19 |
| | 0.10 | 31 |

EXAMPLE 2

Conjugate of Antibody 007B with 4-desacetyl-23-desmethoxyvinblastine, carbonyl-4-benzylidenehydrazide Three conjugation reactions were carried out, under the same conditions except for the input ratio of drug-linker to antibody. In each case, the antibody was 007B, supplied in the form of 0.8 ml of solution in borate buffer at pH 8.6, with a concentration of 12.3 mg of antibody/ml.

The intermediate of Preparation 2 was supplied as a solution in dimethylformamide containing 30 mg/ml of intermediate. The organic solution was added to the antibody solution in each instance, and the reaction mixtures were allowed to stir in the dark for two hours. They were then purified as described in Example 1, with the following results.

A. The amount of vinca-drug intermediate was 0.65 mg, supplied as 0.02 ml of solution; 0.045 ml of additional dimethylformamide was added as well. The product was 5.7 mg of conjugate at a conjugation ratio of 5.7, in the form of 6.5 ml of solution.

B. A 1.3 mg portion of vinca-linker intermediate was used, as 0.04 ml of solution plus 0.025 ml of additional dimethylformamide. The product was 0.7 mg of conjugate, at a conjugation ratio of 7.2 in 5.4 ml of solution.

C. A 1.95 mg portion of intermediate was used, as 0.065 ml of solution. No product was obtained.

The product of Example 2A was tested in tissue culture against the UCLA/P3 adenocarcinoma cell line in a method which determines cytotoxicity against the carcinoma cells by measuring inhibition of $^3$H-leucine incorporation of the cells. The 50% inhibitory concentration of the conjugate was 0.08 μg/ml, the $IC_{50}$ of the intermediate of Preparation 1 was 0.07 μg/ml, and the $IC_{50}$ of 4-desacetyl-23-desmethoxyvinblastine hydrazide was 0.001 μg/ml.

EXAMPLE 3

Conjugate of Antibody 007B with 4-desacetyl-23-desmethoxyvinblastine, carbonyl-4-benzylidenehydrazide A conjugation similar to that of Example 1 was carried out, on a considerably larger scale, starting with 40 ml of antibody solution containing 10 mg of antibody 007B per ml. To the antibody solution was added a solution of the intermediate of Preparation 2, containing 63.8 mg of intermediate in 3.3 ml of dimethylformamide. A 4.8 ml portion of additional dimethylformamide was also added. The reaction mixture was stirred in the dark for 1.5 hours, and was then purified as described in Example 1 to obtain 278 mg of conjugate, at a conjugation ratio of 4.8, in the form of 120 ml of solution in physiological buffered saline. The product was concentrated by vacuum dialysis into physiological buffered saline at pH 7.4 to obtain 18 ml of solution, containing 7.2 mg/ml of conjugate with a conjugation ratio of 4.4.

The conjugate was tested in vivo against UCLA/P3-induced tumors in female nude mice, substantially as described in Example 1. The administration of drug was performed on days 15, 17, 20 and 23 after implantation, and the tumors were measured and the masses were estimated from the formula of Geran et al., *Cancer Chemother. Reports* 3, 1 (1972), on days 27, 34, 41 and 48.

When administration of the conjugate was begun at 15 days, the mean weight of tumors was 1 gram. The tumors in untreated control animals continued to grow steadily, to a mean weight of about 6 grams at 48 days. Administration of doses of 0.5, 1 and 2 mg/kg of vinca drug in the form of the above conjugate regressed the tumors. At the 27 day observation, mean weight of the tumors in all of the treated groups was about 250 mg. At 48 days, the tumors of the 1 and 2 mg/kg treatment groups were still 200 mg or less. At 48 days, the tumors of the 0.5 mg/kg group had grown to the 1 gram weight which they had at the beginning of treatment.

In another experiment, a similar but different batch of the same conjugate was administered to mice which had been implanted with UCLA/P3 xenografts, on day 16, 19, 22 and 25 after implantation. The mean tumor mass was then about 1300 mg. Doses of 0.25 mg/kg (based on vinca hydrazide content) slowed tumor growth but did not regress it. Doses of 0.5, 1 or 2 mg/kg regressed the tumors, so that at 37 days the mean tumor mass of all three treatments was only about 300 mg. The 2 mg/kg treatment held the mean tumor mass constant at that level through 51 days; the tumors of mice receiving 0.5 and 1 mg/kg had a mean mass of about 700 mg at 51 days.

EXAMPLE 4

Conjugate of Antibody L4KS with 4-desacetyl-23-desmethoxyvinblastine, carbonyl-4-benzylidenehydrazide Antibody L4KS, as described by Starling et al., *J. Cell. Biochem. Supp.*, 11B, 1982 (1987), was dialyzed into 0.34M borate buffer at pH 8.6 to obtain a concentration of 11.3 mg/ml. A 10 mg portion of antibody, in that solution, was used, and to it was added 0.78 mg of the intermediate of Preparation 2 as a solution in 0.072 ml of dimethylformamide. The mixture was stirred at ambient temperature for two hours in the dark, and was then centrifuged. The supernatant was chromatographed over a column of Biogel P6 (Bio-Rad Laboratories, Richmond, Calif. 94804), eluting with physiological buffered saline. The product-containing fractions were collected and concentrated under vacuum, and the product was analyzed by ultraviolet analysis, observing the curve at 279 and 293 nm to determine that 8.7 mg of conjugate had been obtained, at a conjugation ratio of 3.2, in the form of a solution containing 1.5 mg/ml. The conjugate was evaluated by determining its cytotoxicity against UCLA/P3 cells in tissue culture. The $IC_{50}$ of the conjugate was 0.024 µg/ml, compared to the $IC_{50}$ of 0.001 µg/ml for 4-desacety-23-desmethoxyvinblastine hydrazide.

EXAMPLE 5

Conjugate of Antibody 14.95.55 with 4-desacetyl-23-desmethoxyvinblastine, carbonyl-4-benzylidenehydrazide A portion of antibody 14.95.55, as described by Corvalan et al., *Protides of Biol. Fluids* 31, 921-24 (1984), was dialyzed into borate buffer at pH 8.6 to obtain 1 ml of solution containing 8.32 mg of antibody. To the solution was added 0.66 mg of the intermediate of Preparation 2, as a solution in 0.08 ml of dimethylformamide. The reaction mixture was stirred in the dark at ambient temperature for 45 minutes, and the mixture was then purified as described in Example 1 above to obtain 3.0 mg of conjugate at a conjugation ratio of 4.8, in the form of 3.7 ml of solution in physiological buffered saline.

The binding capacity of the conjugate was assessed by radioimmunoassay, comparing it with unconjugated antibody. The titration curves of the conjugate and the antibody were substantially similar, indicating that the binding capacity of the antibody was essentially unchanged by conjugation.

EXAMPLE 6

Conjugate of Antibody B72.3 with 4-desacetyl-23-desmethoxyvinblastine, carbonyl-4-benzylidenehydrazide Antibody B72.3 was described by Colcher et al., *Proc. Natl. Acad. Sci. USA*, 78, 199-203 (1981), and is available from the National Cancer Institute. A portion of it was dialyzed into pH 8.6 borate buffer at a concentration of 10 mg/ml. A 5 mg portion of antibody was used in each of three conjugations. In each case, the vinca intermediate was that of Preparation 2, supplied as a solution containing 30 mg/ml. The reactions were run at ambient temperature in the dark for two hours, and the mixtures were purified as described in Example 1 above.

A. An 0.32 mg portion of vinca-linker intermediate was used in the form of 0.01 ml of solution, and 0.02 ml of additional dimethylformamide was added. The product was 2.8 mg of conjugate, at a conjugation ratio of 3.0, in the form of 2 ml of solution.

B. An 0.65 mg portion of intermediate was used, as 0.02 ml of solution and 0.01 ml of additional dimethylformamide was added. The product was 1.2 mg of conjugate, at a conjugation ratio of 4.9, in the form of 2 ml of solution.

C. An 0.97 mg portion of intermediate was used, as 0.03 ml of solution, and the product was 0.5 mg of conjugate, at a conjugation ratio of 6.6, in the form of 2.7 ml of solution.

The product of Example 6C was tested in tissue culture against LS174T adenocarcinoma cells. It was found that the cytotoxic $IC_{50}$ of the conjugate was 0.047 µg/ml, compared to 0.0001 for each of 4-desacetyl-23-desmethoxyvinblastine hydrazide and the intermediate of Preparation 1.

EXAMPLE 7

Conjugate of Antibody KS1/4 S2 with 4-desacetyl-23-desmethoxyvinblastine, carbonyl-4-benzylidenehydrazide A portion of antibody KS1/4 S2, the antigen-binding portion of the antibody described as KS1/4 by Varki et al., *Cancer Research* 44, 681-66 (1984), was dissolved in 0.34M borate buffer at pH 8 in a concentration of 18 mg/ml. Three conjugations were carried out, using 0.56 ml portions of the antibody solution in each. In each instance, the antibody was conjugated with the intermediate of Preparation 2, which was supplied as a dimethylformamide solution containing 43.5 mg/ml of vinca drug. In each instance, the reaction time was 1.5 hours in the dark at ambient temperature. After the reaction, the reaction mixtures were purified as described in Example 1.

A. A 0.015 ml portion of the vinca solution was used, together with 0.03 ml of additional dimethylformamide. The product amounted to 8.2 mg, at a conjugation ratio of 2.1, in the form of 4.8 ml of solution in physiological buffered saline.

B. A 0.03 ml portion of vinca solution was used, with 0.015 ml of additional dimethylformamide. The product was 7.8 mg of conjugate, with a conjugation ratio of 3.6, in the form of 5.2 ml of solution.

C. A 0.045 ml portion of vinca solution was used, to obtain 7.6 mg of conjugate at a conjugation ratio of 5.4 in the form of 5.4 ml of solution.

The binding capacity of the conjugates was determined by radioimmunoassay which showed that the relative binding capacity of product A was 54%, of product B, 48%, and of product C, 37% of the capacity of the native antibody.

PREPARATION 3

Production of L/1C2 Antibodies

Vials of frozen L/1C2 hybridoma are obtained from the American Type Culture Collection, under the accession number HB9682. Viable cells are recovered by thawing the contents of a vial in a 37° C. water bath while swirling the vial. The cell suspension is then diluted 1:2 with balanced salt solution (Grand Island Biological Company (GIBCO), 3175 Staley Road, Grand Island, N.Y. 14072) and the suspension is centrifuged through a serum underlay to partition the cells from the cryogenic medium. The supernatant is aspirated, and the cells in the cell pellet are suspended in culture medium (Ventrex HL-1, Ventrex Laboratories, Portland, Me.) supplemented with 10% fetal calf serum, 2 mM L-glutamine (GIBCO) and 50 μg/ml gentamicin sulfate (GIBCO) in T150 tissue culture flasks in 5% carbon dioxide at 37° C. Supernatants from nearly confluent cultures are collected and residual cells are removed by centrifugation. Antibody is purified from the cell free supernatant by passing over a Protein A Sepharose column (Pharmacia, Uppsala, Sweden). Antibody binds to the column and culture medium is washed free in 0.01M sodium phosphate at pH 8.0. Antibody is then eluted from the column with 0.1M sodium phosphate buffer at pH 3.5. Eluted antibody is immediately neutralized with 1M Trizma buffer (Sigma, St. Louis, Mo.) at pH 7.4 and dialyzed and concentrated in a vacuum dialyzer (BioMolecular Dynamics, Beaverton, Oreg.) containing 0.01M sodium phosphate pH 7.4 plus 0.15M sodium chloride. Antibody preparations are sterilized by filtration through 0.2 μm porous membrane and stored at 4° C. until used.

EXAMPLE 8

Conjugate of Antibody L/1C2 with 4-desacetyl-23-desmethoxyvinblastine, carbonyl-4-benzylidenehydrazide A 10 mg portion of antibody L/1C2, as 0.56 ml of solution in 0.34M borate buffer at pH 8, was added to a vial. To it was added 0.65 mg of the intermediate of Preparation 2, in 0.045 ml of dimethylformamide. The mixture was stirred for 1.5 hours at ambient temperature, and was then centrifuged. The supernatant was purified by chromatography on Sephadex G25, eluting with physiological buffered saline. The product-containing fractions were combined to obtain 1.3 mg of conjugate having a conjugation ratio of 6.2 moles per mole, in 5.4 ml of solution, as determined by ultraviolet analysis.

The product was evaluated against T222 cells in tissue culture. It inhibited the cells' growth by 40% at 0.032 mcg/ml, and by 70% at 0.32 mcg/ml. In comparison, 4-desacetyl-23-desmethoxyvinblastine hydrazide inhibited the growth of the cells by 45% at 0.01 mcg/ml, and by 82% at 0.1 mcg/ml.

PREPARATION 4

3-(4-Formylphenylcarbonylamino)propionic acid, N-succinimido ester

To a 250 ml flask were added 3 g of 4-carboxybenzaldehyde and 2.3 g of N-hydroxysuccinimide in 100 ml of dioxane. The mixture was stirred for 5–10 minutes, and then 4.1 g of dicyclohexylcarbodiimide was added. The mixture was stirred for one hour at ambient temperature, and was then filtered. The filtrate was evaporated under vacuum to obtain 9.4 g of a white solid, which was recrystallized from 25 ml of hot isopropanol. The intermediate product was triturated with propanol to obtain 2.1 g of the desired N-succinimido ester of 4-carboxybenzaldehyde.

Additional batches of intermediate were made, and 10 g total of the above N-succinimido ester was added to a solution of 3.6 g of β-alanine in 40 ml of 1N sodium hydroxide and about 100 ml of water. The pH was kept above 8 while the mixture was stirred for 1.5 hours. The mixture was then filtered, and the filtrate was made acid to pH 1.9 with 2N hydrochloric acid. It was extracted three times with 150 ml total of ethyl acetate, and the organic layers were combined and washed with brine. The organic layer was then dried over sodium sulfate and evaporated under vacuum to obtain 4.6 g of a white solid, 3-(4-formylphenylcarbonylamino)-propionic acid.

One hundred mg of the above intermediate, 103 mg of dicyclohexylcarbodiimide, 57.5 g of N-hydroxysuccinimide and 10 ml of dioxane were added to a small flask, and the mixture was stirred at ambient temperature under nitrogen. The progress of the reaction was observed by thin layer chromatography, and 75 mg of additional dicyclohexylcarbodiimide and 45 mg of additional N-hydroxysuccinimide were added. After four hours, the reaction mixture was filtered, and the filtrate was evaporated to a solid under vacuum. About 200 mg of impure product was obtained, which was chromatographed on 30 g of silica gel, eluting with 5% isopropanol in dichloromethane. The product-containing fractions were combined and evaporated to obtain 81 mg of the desired intermediate in somewhat impure form.

PREPARATION 5

Antibody L/1C2 F(ab')₂ Fragment

The F(ab')₂ fragment of antibody L/1C2 was prepared by adding 2.4 ml of pepsin solution, containing 12.6 mg of pepsin/ml, to 1.5 g of L/1C2 antibody in 270 ml of physiological buffered saline. The mixture was held at 37° C. for 2 hours and 20 minutes, and then the reaction was stopped by the addition of triethanolamine. The product was then concentrated by chromatography on a Fast Flow Sepharose (Pharmacia) column, eluting with 0.15M sodium acetate. The F(ab')₂-containing fractions were combined, and concentrated by dialysis to obtain 100 ml of product solution containing 992 mg of the F(ab')₂ fragment of antibody L/1C2.

PREPARATION 6

Antibody L/1C2 F(ab')₂ Fragment, 3-(4-formylphenylcarbonylamino)propionyl Derivative L/1C2 F(ab')₂ fragment, prepared in Preparation 5, was dialyzed into 0.34M borate buffer at pH 8.6 to obtain 23 mg of F(ab')₂ fragment in the form of 3.8 ml of solution. That solution was combined with 0.44 mg of 3-(4-formylphenylcarbonylamino)propionic acid, N-succinimido ester, in 102 μl of acetonitrile. The mixture was stirred for one hour at ambient temperature, and the solution was then chromatographed over a column of 11 g of Sephadex G25, eluting with 0.1M sodium acetate at pH 5.6. The product-containing fractions were combined to obtain 19 mg of derivatized antibody fragment, at a conjugation ratio of 2.8 moles per mole, in 9.6 ml of solution.

EXAMPLE 9

Conjugate of L/1C2 F(ab')₂ Fragment with 4-desacetyl-23-desmethoxyvinblastine, propionyl-3-aminocarbonyl-4-benzylidenehydrazide An 8 mg portion of the intermediate prepared in Preparation 6 was added to 6.9 mg of solid 4-desacetyl-23-desmethoxyvinblastine, hydrazide. The pH was adjusted to 5.6 by adding dilute hydrochloric acid, and the mixture was stirred at ambient temperature for 21 hours. The mixture was then centrifuged, and the supernatant was chromatographed over a column of 11 g of Sephadex G25 eluting with physiological buffered saline. The product-containing fractions were combined and filtered to obtain 4.8 ml of product solution which was found by uv analysis, observing the curve at 280 and 325 nm, to contain 3.5 mg of conjugate at a conjugation ratio of 3.5 moles of vinca drug per mole of antibody fragment.

The conjugate's cytotoxicity against T222 cells in tissue culture was determined as previously described. It had no effect at 0.1 μg/ml, based on content of vinca hydrazide, and inhibited growth by 85% at 1 μg/ml.

PREPARATION 7

Antibody 14.95.55, 3-(4-formylphenylcarbonylamino)-propionyl Derivative

A portion of antibody 14.95.55 was dialyzed into 0.34M borate buffer at pH 8.6, to obtain a solution containing 11.6 mg/ml of antibody. A 3.9 ml portion of the solution, containing 45.2 mg of antibody, was added to a 10 to a 10 ml flask, and to it was added 132 μl of a solution containing 0.57 mg of the intermediate of Preparation 4, dissolved in acetonitrile. The mixture was stirred one hour at ambient temperature, and was then chromatographed over a 10 g column of Sephadex G25, eluting with 0.1M sodium acetate at pH 5.6. The product-containing fractions were filtered and analyzed by ultraviolet, observing peaks at 258 and 280 nm. A yield of 40 mg of derivative was obtained, as a solution containing 2.6 mg/ml. The conjugation ratio was 4.1 moles of linker per mole of antibody.

EXAMPLE 10

Conjugate of Antibody 14.95.55 with 4-desacetyl-23-desmethoxyvinblastine, propionyl-3-aminocarbonyl-4-benzylidenehydrazide A 14.75 ml portion of the intermediate solution of Preparation 7, containing 38.3 mg of modified antibody, was added to a flask, and 2.6 ml of 1M phosphate buffer was added, followed by 22.2 mg of 4-desacetyl-23-desmethoxyvinblastine hydrazide sulfate. The mixture was stirred overnight at ambient temperature, and it was then centrifuged for 15 minutes and chromatographed on a column of 45 g of Sephadex G25, eluting with physiological buffered saline. Analysis of the product-containing fractions by ultraviolet, observing the curve at 280 and 325 nm, showed that 21.8 mg of conjugate was obtained, at a conjugation ratio of 3.8 moles of drug per mole of antibody.

The conjugate was tested in tissue culture against UCLA/P3 cells. Its 50% inhibitory concentration was 0.035 μg/ml based on vinca hydrazide content.

A similar but different batch of the same conjugate was tested against tumors induced by xenografts of LS174T colon carcinoma cells in female Charles River nude mice. The conjugate was administered intravenously on days 9, 11, 14 and 17 after implantation, when the mean tumor mass was about 1000 mg. Doses of 0.25 mg/kg (based on vinca hydrazide content) slowed growth of the very fast-growing tumors only slightly; at 28 days, tumors of the control mice weighed 10 g. The mean mass of tumors in mice given 0.5 mg/kg was about 4.5 g, and the mean mass of tumors in mice given 1 mg/kg was about 1 g, essentially unchanged from the start of treatment.

PREPARATION 8

4-desacetyl-23-desmethoxyvinblastine, 4-carboxymethoxy-α-methylbenzylidenehydrazide One g of 4-desacetyl-23-desmethoxyvinblastine hydrazide was dissolved in 75 ml of tetrahydrofuran, and 1.52 g of 4-acetylphenoxyacetic acid was added. Ten ml of dimethylformamide and 5 g of sodium sulfate were added, and the reaction was stirred overnight at ambient temperature under anhydrous conditions. The reaction mixture was filtered, and the filtrate was evaporated under vacuum to obtain a solid residue, which was purified by high performance liquid chromatography on silica gel, eluting with a linear gradient changing from 5% to 50% methanol in ethyl acetate.

Concentration of the product-containing fractions yielded 490 mg of the desired intermediate, which was identified by mass spectroscopy which showed molecular ions of weight 900, 944, 957 and 973.

PREPARATION 9

4-desacetyl-23-desmethoxyvinblastine, 4-succinimidoxycarbonylmethoxy-α-methylbenzylidenehydrazide A 300 mg portion of the intermediate of Preparation 8 was dissolved in 25 ml of dimethylformamide and the solution was cooled in an ice bath, under nitrogen. To it was added 86 μl of N-methylmorpholine, and the mixture was stirred for 20 minutes. Then 81 μl of isobutyl chloroformate was added, and the mixture was stirred 20 minutes more. Then 108 mg of N-hydroxysuccinimide was added and the mixture was stirred overnight while it gradually warmed to ambient temperature. The volatiles were then removed under vacuum, and the residue was taken up in dichloromethane and washed with brine. The organic layer was dried with sodium sulfate and evaporated under vacuum to obtain 110 mg of the desired active ester.

EXAMPLE 11

Conjugate of Antibody 007B with 4-desacetyl-23-desmethoxyvinblastine, carbonylmethoxy-α-methyl-4-benzylidenehydrazide Antibody 007B was dialyzed into 0.34M borate buffer at pH 8.6, at a concentration of 4.05 mg of antibody/ml. Two conjugations were carried out, using different amounts of the intermediate of Preparation 9. In each case, the amount of antibody was 12.15 mg. supplied as 3 ml of antibody solution. The reactions with the antibody were carried out for one hour at ambient temperature, after which the reaction mixtures were centrifuged, and the supernatant was purified by chromatography over a Sephadex G25 column, eluting with physiological buffered saline. The product-containing fractions were analyzed by ultraviolet analysis, observing the curves at 279 and 285 nm.

A. A 4.2 mg portion of the intermediate of Preparation 9 was used, dissolved in 240 μl of dimethylformamide. The product was 6 mg of conjugate, at a conjugation ratio of 5.2 moles per mole, in the form of 7.5 ml of solution.

B. The amount of the intermediate was 6.3 mg, dissolved in 240 μl of dimethylformamide, and 1.56 mg of product conjugate was obtained, having a conjugation ratio of 11.4, in the form of 6 ml of solution.

The product of conjugation A was evaluated against UCLA/P3 adenocarcinoma cells in tissue culture, in the cytotoxicity test which has been described previously. It was found that the conjugate inhibited growth of the cells by 29% at a concentration of 50 ng/ml, and by 93% at a concentration of 100 ng/ml. The activity of the unconjugated intermediate of Preparation 8 was essentially the same in the cytotoxicity test.

PREPARATION 10

4-desacetyl-23-desmethoxyvinblastine, 4-carboxymethoxybenzylidenehydrazide

A process essentially like that of Preparation 8 was carried out, using 940 mg of 4-formylphenoxyacetic acid. The product was 170 mg of the desired intermediate, which showed molecular ions in mass spectroscopy of weight 886, 944 and 958.

PREPARATION 11

4-desacetyl-23-desmethoxyvinblastine, 4-succimidoxycarbonylmethoxybenzylidenehydrazide A process like that of Preparation 9 was carried out, starting with 500 mg of the intermediate of Preparation 10, 145 μl of N-methylmorpholine, 137 μl of isobutyl chloroformate and 182 mg of N-hydroxysuccinimide. The product was 160 g of the desired active ester.

EXAMPLE 12

Conjugate of Antibody 007B with 4-desacetyl-23-desmethoxyvinblastine, carbonylmethoxy-4-benzylidenehydrazide Two conjugations were carried out, using the intermediate of Preparation 11, under conditions identical with those of Example 11. The product of conjugation A was 6.6 mg of conjugate having a conjugation ratio of 3.5 moles per mole, in the form of 5.8 ml of solution. The product of conjugation B was 6.0 mg of conjugate, having a conjugation ratio of 4.8 moles per mole, in the form of 7.2 ml of solution.

The product of conjugation A was evaluated against UCLA/P3 cells in tissue culture, and was found to inhibit growth by 33% at 100 ng/ml, and by 100% at 250 ng/ml. The cytotoxic activity of the intermediate of Preparation 10 was essentially the same.

PREPARATION 12

3-(5-Formylpyrrol-2-ylcarbonylamino)propionic acid, N-succinimido ester

To a flask were added 139 mg of 5-formylpyrrol-2-ylcarboxylic acid, 247 mg of dicyclohexylcarbodiimide, 138 mg of N-hydroxysuccinimide and 10 ml of dimethylformamide. The mixture was stirred for two hours at ambient temperature under nitrogen, and the solvent was removed under vacuum to obtain 394 mg of crude active ester.

The above residue was taken up in 1 ml of acetonitrile. Not all of the residue went into solution. The heterogeneous mixture was added slowly to a solution of 89 mg of β-alanine in 2 ml of 0.5N sodium hydroxide. Concurrently, 1N sodium hydroxide was added to maintain the pH between 7.5 and 8.0. The mixture was then stirred at ambient temperature for 1 hour, and was filtered. The filtrate was made acid with dilute hydrochloric acid, was saturated with sodium chloride, and was extracted with ethyl acetate. It was then dried and concentrated to an orange oil, which was chromatographed on a silica gel column, eluting with 10% methanol in dichloromethane. The product-containing fractions were concentrated under vacuum to obtain 49 mg of 3-(5-formylpyrrol-2-ylcarbonylamino)propionic acid.

A 31 mg portion of the above intermediate was taken up in 3 ml of dioxane, and to it was added 35 mg of dicyclohexylcarbodiimide and 19 mg of N-hydroxysuccinimide. The mixture was stirred for 2 hours at ambient temperature under nitrogen, and was then filtered and concentrated under vacuum. The residue was chromatographed on silica gel, eluting with 5% methanol in dichloromethane to obtain about 6 mg of the desired intermediate active ester.

PREPARATION 13

Antibody 007B, 3-(5-formylpyrrol-2-ylcarbonylamino)-propionyl derivative

A 105 mg portion of antibody 007B, in the form of a solution containing 15 mg/ml in 0.34M borate buffer, was combined with 300 μl of a solution of the intermediate of Preparation 12 containing 1.29 mg of the intermediate active ester in acetonitrile. The mixture was stirred for 1 hour at ambient temperature, and was then chromatographed over a 10 g column of Sephadex G25, eluting with 0.1M sodium acetate at pH 5.6. The product-containing fractions were combined and analyzed by ultraviolet spectroscopy, observing the curve at 280 and 300 nm. The product comprised 14.6 ml of solution, at a concentration of 5.7 mg/ml, a total of 83.2 mg of the intermediate named above. The conjugation ratio was 3.6.

EXAMPLE 13

Conjugate of Antibody 007B with 4-desacetyl-23-desmethoxyvinblastine, propionyl-3-aminocarbonyl-2-pyrrol-5-methylidenehydrazide A 36 mg portion of 4-desacetyl-23-desmethoxyvinblastine hydrazide sulfate was added to 60 mg of the intermediate of Preparation 13, in 12.4 ml of pH 5.6 buffer containing 0.1M sodium acetate and 0.15M phosphate ion. The mixture was stirred in the dark for 24 hours, and was centrifuged. The supernatant was chromatographed on 17 g of Sephadex G25, and the product-containing fractions were combined and analyzed by ultraviolet spectroscopy, measuring the absorbance at 340 and 280 nm. It was found that 43.8 mg of conjugate was obtained, with a conjugation ratio of 5.4 moles of vinca drug per mole of antibody, as 15.8 ml of solution.

The conjugate was subjected to radioimmunoassay to compare its ability to bind to antigen with the binding of free antibody. It was found that the conjugation had reduced the antibody's binding ability only slightly. It was tested in vitro against UCLA/P3 cells, where its 50% inhibitory concentration was 0.0001 $\mu$g/ml (based on vinca hydrazide content).

PREPARATION 14

Antibody 007B,
3-(4-formylphenylcarbonylamino)propionyl derivative

A 7.0 ml portion of antibody 007B solution, containing 15 mg/ml of antibody in 0.34M borate buffer at pH 8.6, was combined with 1.33 mg of the intermediate of Preparation 4, as a solution in 0.31 ml of acetonitrile. The reaction mixture was stirred for 1 hour at ambient temperature, and was then chromatographed on 10 g of Sephadex G25, eluting with 0.1M sodium acetate buffer at pH 5.6. The product-containing fractions were collected and analyzed by ultraviolet, measuring absorbance at 258 and 280 nm. It was found that the concentration was 5.1 mg/ml of conjugate having a conjugation ratio of 4.3. The total yield of conjugate was 91 mg.

EXAMPLE 14

Conjugate of Antibody 007B with 4-desacetyl-23-desmethoxyvinblastine, propionyl-3-aminocarbonyl-4-benzylidenehydrazide A 36 mg portion of 4-desacetyl-23-desmethoxyvinblastine, hydrazide sulfate was added to 13.8 ml of a solution containing 60 mg of the intermediate of Preparation 14 in 0.1M sodium acetate buffer. The mixture was stirred at ambient temperature for 24 hours, and was then centrifuged and chromatographed on 17 g of Sephadex G25. The product-containing fractions were collected and filtered through 0.22 $\mu$m porous membrane to obtain 21.9 ml of product solution, containing 2.0 mg of conjugate per ml by ultraviolet spectroscopy, measuring absorbance at 280 and 293 nm. The conjugation ratio was 4.1 moles of vinca drug per mole of antibody.

The conjugate was tested against tumors induced in female nude mice by xenografts of UCLA/P3 adenocarcinoma. The conjugate was injected at 0.5 mg/kg, based on vinca drug content, on days 16, 19, 22 and 25 after implantation. On day 16, the mean tumor mass of the treated animals was about 500 mg. The tumors were regressed by the treatment, and at 51 days, the mean tumor mass was only about 50 mg. Tumors in the untreated control animals grew steadily to a very large size, as this tumor consistently does.

Compositions and Methods of Use

The conjugates of the present invention are useful in the method of inhibiting the growth of unwanted cells which is an important part of the present invention. Accordingly, the invention also includes a pharmaceutical composition, most preferably a parenteral composition suitable for injection into the body of the patient. Such compositions are formulated by methods which are commonly used in pharmaceutical chemistry. The present conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as lactose, to allow the dried preparation to dissolve quickly upon reconstitution. Such formulations are reconstituted with highly purified water to a known concentration.

The conjugates and the above pharmaceutical compositions are used to inhibit the growth of unwanted cells, making use of the cytotoxic properties of the vinca drugs comprised by the conjugates. Accordingly, the range of uses of the conjugates is determined by the cytotoxic properties of the vinca drugs. The antibody section of this document discusses some of the types of unwanted cells against which the present conjugates may be used advantageously by use of an antibody which targets the cell. Preferably, the present conjugates and compositions are used to inhibit the growth of cancer cells.

The optimum dosage and administration schedule of conjugates of the present invention must be determined by the treating physician, in the light of the patient's condition. It is customary, of course, to administer cytotoxic drugs in the form of divided doses, with intervals of days or weeks between each series of doses. The present conjugates are effective over a wide dosage range, and dosages per week will usually fall within the range from about 0.1 to about 10 mg/kg of conjugate, more preferably in the range from about 0.25 to about 4 mg/kg.

We claim:

1. A cytotoxic drug conjugate of the formula

wherein Ab is a physiologically-acceptable antibody or antigen-recognizing fragment thereof, which recognizes an antigen associated with an undesirable cell;

m is an integer from 1 to about 10;

Z is hydrogen or $C_1$–$C_3$ unbranched alkyl;

X is a bond, $C_1$–$C_4$ alkylene, $C_2$–$C_4$ alkenylene, or amino-$C_1$–$C_4$ alkylene;

Y is a bond, carbonyl, —O—, —S—, or sulfonyl, provided that Y is carbonyl or sulfonyl when X is aminoalkylene, and that Y is a bond or carbonyl when X is a bond;

Ar is pyrrolyl, m-phenyl, or p-phenyl, which phenyl groups may be mono- or disubstituted with bromo, chloro, fluoro, methoxy, nitro or $C_1$–$C_3$ alkyl;

V is a vinca drug of the formula

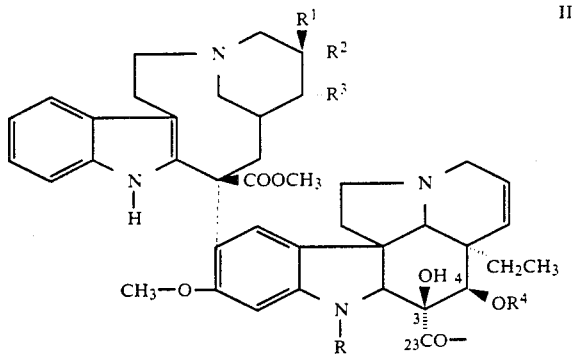

II wherein R is H, CH₃ or CHO; when R² and R³ are taken singly, R³ is H, and one of R¹ and R² is ethyl and the other is H or OH; when R² and R³ are taken together with the carbons to which they are attached, they form an oxirane ring in which case R¹ is ethyl; R⁴ is H, (C₁-C₃ alkyl)-CO, or chlorosubstituted (C₁-C₃ alkyl)-CO.

2. A conjugate of claim 1 wherein the antibody is a monoclonal or chimeric antibody or an antigen-recognizing fragment thereof.

3. A conjugate of claim 2 wherein m is from about 3 to about 8.

4. A conjugate of claim 3 wherein Z is hydrogen or methyl.

5. A conjugate of claim 4 wherein X is a bond or amino-C₁-C₃ alkylene.

6. A conjugate of claim 4 wherein Y is a bond, carbonyl or oxygen.

7. A conjugate of claim 6 wherein Ar is phenyl, mono-substituted phenyl or pyrrolyl.

8. A conjugate of claim 1 wherein Ar is phenyl, mono-substituted phenyl or pyrrolyl.

9. A conjugate of claim 8 wherein X is a bond or amino-C₁-C₃ alkylene.

10. A conjugate of claim 8 wherein Y is a bond, carbonyl or oxygen.

11. A conjugate of claim 10 wherein m is from about 3 to about 8.

12. A conjugate of claim 11 wherein Z is hydrogen or methyl.

13. A conjugate of claim 12 wherein the antibody or fragment thereof recognizes a cancer cell.

14. A conjugate of claim 13 wherein the

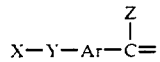

group is 4-benzylidenyl.

15. A conjugate of claim 13 wherein the

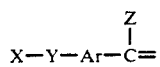

group is 1-(4-methylidenylbenzamido)ethylenyl.

16. A conjugate of claim 12 wherein the antibody is L/1C2.

17. The conjugate of claim 16 which is the conjugate of L/1C2 with 4-desacetyl-23-desmethoxyvinblastine, carbonyl-4-benzylidenehydrazide.

18. A pharmaceutical composition comprising a conjugate of claim 1 and a parenterally administrable medium.

19. A composition of claim 18 wherein the

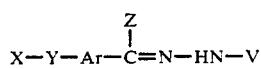

portion of the conjugate is 4-desacetyl-23-desmethoxyvinblastine, 4-benzylidenehydrazide.

20. A composition of claim 18 wherein the

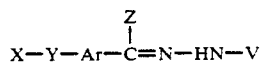

portion of the conjugate is 4-desacetyl-23-desmethoxyvinblastine, 4-ethylaminocarbonyl benzylidenehydrazide.

21. A method of controlling the growth of undesirable cells comprising parenterally administering a conjugate of claim 1 to the patient in need of such treatment.

22. A method of claim 21 wherein the undesirable cells are cancer cells.

* * * * *